United States Patent [19]
Wilson et al.

[11] 4,383,836
[45] May 17, 1983

[54] METHOD FOR TREATING AN AQUEOUS ETHANOL MIXTURE

[75] Inventors: James R. Wilson, Missouri City; Norman I. Anzarut; Wheeler C. Crawford, both of Houston, all of Tex.

[73] Assignee: Texaco Inc., White Plains, N.Y.

[21] Appl. No.: 152,947

[22] Filed: May 23, 1980

[51] Int. Cl.³ ............................................... C10L 1/02
[52] U.S. Cl. ....................................................... 44/56
[58] Field of Search ..................... 44/56; 568/899, 916

[56] References Cited

U.S. PATENT DOCUMENTS 3,455,664  7/1969  Rosscup et al. ..................... 44/56

*Primary Examiner*—Patrick Garvin
*Assistant Examiner*—Y. Harris-Smith
*Attorney, Agent, or Firm*—Carl G. Ries; Robert A. Kulason; James J. O'Loughlin

[57] ABSTRACT

A method is provided for treating an ethanol mixture containing a substantial amount of water comprising admixing said aqueous ethanol mixture with a hydrocarbon fraction containing a substantial amount of an aliphatic olefin having from 3 to 5 carbon atoms and contacting said admixture with an acidic ion exchange resin catalyst to convert the water in said admixture to an oxygenated organic compound.

1 Claim, No Drawings

METHOD FOR TREATING AN AQUEOUS ETHANOL MIXTURE

BACKGROUND OF THE INVENTION

1. Field of the Invention

Because of a perceived shortage of crude mineral oil from which to manufacture motor fuel or gasoline, significant industry efforts have been made to expand the supply of liquid motor fuel by manufacturing gasohol, which is a mixture of ethyl alcohol and of hydrocarbons boiling in the motor fuel boiling range. The ethyl alcohol employed in the manufacture of gasohol is generally obtained from the fermentation of grains or starchy raw materials. The production of ethyl alcohol by means of the fermentation of the noted raw materials results in the production of a relatively impure ethyl alcohol mixture containing a substantial amount of water.

Impure ethyl alcohol containing a substantial amount of water is not suitable for use in the manufacture of a gasohol fuel composition. The reason is that the three components of this normally liquid composition are not mutually soluble under all conditions of temperature and concentration variables. This fuel composition will separate into two phases under some conditions and the resultant two phase fuel supply will have an adverse effect on the operation of an internal combustion engine. It is a conventional practice to refine the crude ethyl alcohol by various treating means, such as by distillation to remove substantially all of the water therefrom in order to blend a relatively dry, i.e. less than about 0.5 weight percent water-containing ethanol. However, this procedure is relatively energy intensive and some observers question the energy conservation effectiveness of producing a gasohol fuel composition.

It is an object of the present invention to provide a novel method for treating ethanol containing substantial amounts of water.

Another object of the invention is to provide a method for upgrading crude ethanol for use in a gasohol mixture.

Another object of the invention is to provide a method for converting a substantial amount of the water content in a methanol mixture to an oxygenated organic compound compatible with a gasohol fuel composition.

It is a further object of this invention to provide an energy conserving method for treating a water-containing ethanol mixture.

The objects of this invention are realized in a method for treating an aqueous ethanol mixture which comprises mixing said aqueous ethanol mixture with a hydrocarbon fraction containing a substantial proportion of an aliphatic olefin having from 3 to 5 carbon atoms to form an ethanol-hydrocarbon fraction admixture, and contacting said ethanol-hydrocarbon fraction admixture with an acidic ion exchange resin catalyst to convert a substantial proportion of said contained water to an oxygenated compound.

DESCRIPTION OF THE PRIOR ART

U.S. Pat. No. 3,793,379, 2,813,908, 2,645,621, and British Pat. No. 1,381,455 disclose ion exchange resin hydration catalysts and methods for hydrating olefins with an ion exchange resin catalyst. The disclosures of these patents are incorporated herein by reference.

SUMMARY OF THE INVENTION

This invention relates to a process for treating a crude ethanol mixture or solution containing a substantial amount of water by mixing the water-containing ethanol with a liquid hydrocarbon mixture containing a substantial amount of olefins having from 3 to 5 carbon atoms and then contacting the admixture with an acidic ion exchange resin catalyst under conditions effective to convert a substantial portion of said water to an oxygenated organic compound. More particularly, the invention relates to a process for improving the quality of an aqueous ethanol mixture containing from about 1 to 10 weight percent or more of water by mixing the aqueous ethanol with a hydrocarbon feed stream containing at least about 25 percent of a $C_3$ to $C_5$ aliphatic olefin and reacting the mixture with a sulfonated ion exchange resin catalyst in order to convert a substantial amount of the water to an oxygenated organic compound, such as an alcohol or ether counterpart of the olefin employed.

DESCRIPTION OF THE PREFERRED EMBODIMENTS

The crude ethanol or crude ethyl alcohol which is improved by the process of this invention is an ethyl alcohol mixture produced by the fermentation of a wide variety of natural materials. Grain or ethyl alcohol has been produced from the fermentation of corn, wheat, sugar cane, potatoes and other cultivated grains and starchy materials as well as from some uncultivated natural materials, such as wood chips. In general, the fermentation process results in the production of a crude ethyl alcohol mixture containing a substantial amount of water generally ranging from about 1 to 10 percent or more. Because of its high water content, crude ethyl alcohol is not well suited for use in the manufacture of gasolhol. Gasohol is a liquid fuel composition generally comprising about 90 percent by weight of a mixture of hydrocarbons boiling in the gasoline boiling range and about 10 weight percent of ethyl alcohol. In order to upgrade crude ethyl alcohol to make it suitable for use in gasohol production, the crude aqueous ethanol is conventionally subjected to a separation treatment, such as distillation, to reduce the water content of the ethanol to an amount ranging from about 0.5 weight percent to 0.1 weight percent or less, the lower the better.

In accordance with the process of the invention, a crude ethanol mixture containing from 1 to 10 percent or more of water is mixed with a hydrocarbon fraction containing a substantial amount of an aliphatic olefin having from 3 to 5 carbon atoms and the resulting admixture is contacted with an acidic ion exchange resin catalyst under suitable conditions to effect a reaction between the contained water and the olefin in the mixture. This reaction produces oxygenated organic compounds, such as lower aliphatic alcohols or ethers or mixtures thereof, from the chemical combination of the water and the olefin and results in the production of an ethyl alcohol-containing reaction product having a substantially reduced water content which is more suitable for use in the manufacture of a gasohol fuel composition.

The distillate hydrocarbon fraction employed in this process broadly comprises a mixture of hydrocarbons in the gasoline boiling range, i.e., having from about 4 to 8 carbon atoms, which also contains a substantial amount of an aliphatic monoolefin having from 3 to 5 carbon atoms. Examples of suitable olefins in this hydrocarbon fraction includes t-amylene, the butenes, such as isobutylene, butene-1, butene-2, and propylene. In general, the olefin should constitute at least 30 weight percent up to 90 weight percent or more of the hydrocarbon fraction. A suitable hydrocarbon fraction for this purpose is one containing from about 40 to 60 percent of the $C_3$ to $C_5$ aliphatic olefin.

An example of a specific hydrocarbon fraction for the process of the invention is a refinery butane-butene stream which can contain from 40 to 60 percent of a mixture of $C_4$ olefins including butene-1, butene-2 and isobutylene. A preferred $C_4$ olefin will consist of a mixture of butanes and from 40 to 50 percent of isobutylene.

Another suitable hydrocarbon fraction for this process is a mixture of $C_3$ hydrocarbons consisting of propane and propylene. A useful $C_3$ feed stream will consist of 40 to 90 percent or more of propylene, the balance being propane.

The crude aqueous ethanol and the prescribed hydrocarbon fraction are blended to provide a mixture having at least about a 1:1 mole ratio of said olefin to the water in the resulting mixture. Preferably, the crude ethanol and hydrocarbon fraction should be combined so as to provide a mixture having a substantial molar excess of the olefin component as compared to the water component in the mixture. Broadly, a molar ratio of from 1 to 5 moles of olefin or more per mole of water can be employed in the process of the invention. Preferably, the mole ratio of the olefin to the water should range from about 1.5 to 3.

The process of the invention is conducted by contacting the prescribed mixture of aqueous ethanol and hydrocarbon fraction with an acid organic ion exchange resin catalyst under suitable conditions of temperature and pressure to effect a reaction between the water and the olefinic components of the feed stream to form at least one oxygenated organic compound.

The ion-exchange resins suitable as a catalyst in the present invention can be generically defined as synthetic aryl resins possessing essentially a hydrocarbon skeleton combined with strong mineral acid groups. These ion exchange resins must be capable of being at least slightly swelled by water at the hydration temperature used but have a molecular weight high enough or a sufficiently cross-linked structure to be substantially insoluble in water at temperatures up to about 400° F. and contain as much as two acid groups, preferably sulfonate groups per benzene ring. The resins may be prepared in a variety of ways. For example, sulfonation or equivalent acid treatment can be applied either to a monomer such as styrene which is subsequently polymerized into a suitable high molecular weight ion exchange resin or, preferably, the organic resin may be formed first and the acid groups introduced by treating the solid resin in a suitable form.

Examples of resins particularly suitable for the purpose of the present invention include solid cross-linked polymers of vinyl aromatic compound such as styrene or vinyl toluene, or cross-linked copolymers of the vinyl aromatic compound with other monoethenically unsaturated compounds such as isobutylene, acrylonitrile or its homologs, acrylamide or its homologs and methylacrylate or methacrylate or its higher alkyl homologs.

The preferred catalysts for the purpose of the present invention are prepared from resinous copolymers of styrene containing a minor amount of p-divinylbenzene combined therewith, such resins containing from about 88 to 96 percent styrene copolymerized with from 12 to 4 percent of divinylbenzene.

The active catalyst is prepared by taking prescribed solid cation-exchange resin and converting it to a sulfonated or phosphonated form according to known methods in order to introduce from about 0.25 to 3, preferably from about 0.5 to 2 inorganic acid radicals per benzene nucleus of the polymeric resin. Suitable sulfonating agents include concentrated or fuming sulfuric acid, chlorosulfonic acid, and sulfur trioxide in nitrobenzene. An excess of the sulfonating agent is used. The sulfonation is effected at a temperature between about $-20°$ and 200° C.

Numerous polystyrene type ion exchange resin catalysts are commercially available. Dowex 50X8 is a sulfonated resinous copolymer of about 92 percent styrene and 8 percent divinylbenzene containing about 44 to 50 percent moisture and about 12 to 60 percent sulfur in a sulfonate form obtainable from the Dow Chemical Company. A similar group of sulfonated ion exchange resin catalysts are commercially available from the Rohm & Haas Company under the Amberlite trademark.

The process of the invention is conducted by contacting the feed stream admixture consisting of aqueous ethanol and hydrocarbon fraction containing aliphatic olefins with the prescribed acid form of the ion exchange resin catalyst. The reaction temperature for effecting the conversion of the water and olefinic components of the feed mixture into the desired oxygenated organic compounds is a temperature ranging from about 125° to about 400° F. It is preferred, however, to effect the reaction at a temperature ranging between about 225° F. to about 350° F. with a particularly preferred reaction temperature being in the range of 260° to 330° F.

This reaction is conducted under pressure to keep a substantial proportion of the reactants in the liquid phase. The reaction pressure can range from about 20 to 200 atmospheres with the preferred reaction pressure ranging from about 60 to 125 atmospheres. Particularly preferred reaction conditions are a pressure of 100 atmospheres and a temperature of 275° F.

The reaction is generally conducted over a packed bed of granular particles of catalyst disposed in a tube or in a tower-like reactor. The reaction mixture can be passed through the catalyst bed in an upward or downward flow direction when the catalyst is supported within a tower-like reactor.

The following example(s) illustrate the practice of this invention.

EXAMPLE I

An aqueous ethanol mixture, containing about 10% water derived from the fermentation of corn, is admixed with a butane-butene hydrocarbon fraction, containing about 40% of butenes, in suitable proportions, to form an admixture in which the mole ratio of butenes to water is about 1.5. The reaction admixture is heated to about 275° F. and is brought under a pressure of about 100 atmospheres. The mixture is contacted with an acidified ion exchange resin catalyst by passing the liquid mixture downwardly over a packed bed of the catalyst in a tower reactor. The catalyst used is Dowex 50X8 which is an ion exchange resin solid copolymer of about 92% styrene and 8% divinylbenzene sulfonated to contain about 40% sulfonic acid groups on a dry basis employed in the hydrogen (acid) form. The reaction mixture is passed over the catalyst bed at a rate of 100 grams of reaction mixture per liter of catalyst per hour. The reaction product which issues from the reactor is improved by the conversion of a substantial amount of the water and olefin components to oxygenated organic compounds yielding a reaction product which is suitable for blending into a mixture of hydrocarbons boiling in the gasoline boiling range to produce gasohol.

EXAMPLE II

An aqueous ethanol mixture containing about 7% water derived from the fermentation of sugar cane is admixed with a propane-propylene fraction containing about 50% propylene in proportions to form an admixture in which the mole ratio of propylene to water is about 2 to 1. This reaction mixture is heated to about 285° F. and brought under pressure of about 110 atmospheres. This mixture is contacted with Amberlyst 15 which is a sulfonated ion exchange resin catalyst produced by Rohm & Haas. The reaction mixture is passed downwardly through the catalyst bed at a rate of 100 grams of the reaction mixture per liter of catalyst per hour. The reaction product issuing from the reactor is improved by the conversion of a substantial amount of the water and propylene component to isopropyl alcohol and this reaction product is suitable for blending into a mixture of hydrocarbons boiling in the gasoline boiling range to produce gasohol.

EXAMPLE III

An aqueous ethanol mixture containing about 12 weight percent water derived from the conversion of wood waste products is admixed with a hydrocarbon fraction consisting of about 50 weight percent of a mixture of $C_4$ to $C_7$ aliphatic hydrocarbon and 50 weight percent of isobutylene to form an admixture in which the mole ratio of isobutylene to water is about 2.5 to 1. This mixture is reacted as described in Example I above to produce an upgraded ethanol mixture containing oxygenated organic compounds suitable for blending into a gasohol fuel composition.

We claim:

1. A method for preparing a component of a gasohol fuel composition from a crude ethanol mixture containing from about 1 to 10 weight percent of water which comprises mixing said crude ethanol mixture with a hydrocarbon fraction comprising a substantial proportion of an aliphatic olefin having from 3 to 5 carbon atoms and a mixture of hydrocarbons in the gasoline boiling range to form an ethanol-hydrocarbon admixture, and contacting said ethanol-hydrocarbon admixture with an acidic ion exchange resin catalyst under effective olefin hydration conditions to convert a substantial proportion of said water to an oxygenated organic compound and form an upgraded ethanol-hydrocarbon fraction admixture suitable for use in gasohol manufacture.

* * * * *